(12) United States Patent
Sonoura

(10) Patent No.: US 8,571,301 B2
(45) Date of Patent: Oct. 29, 2013

(54) ALIGNMENT METHOD AND EXAMINATION APPARATUS

(75) Inventor: Takafumi Sonoura, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 131 days.

(21) Appl. No.: 13/035,360

(22) Filed: Feb. 25, 2011

(65) Prior Publication Data

US 2012/0076410 A1    Mar. 29, 2012

(30) Foreign Application Priority Data

Sep. 24, 2010 (JP) ................................ 2010-213574

(51) Int. Cl.
*G06K 9/00* (2006.01)
*G06K 9/32* (2006.01)

(52) U.S. Cl.
USPC ............ 382/151; 382/284; 382/294; 382/145

(58) Field of Classification Search
USPC .............. 382/141, 144, 151, 173, 294, 295; 250/310, 306, 307, 311, 397, 492.2, 250/492.3
See application file for complete search history.

(56) References Cited

U.S. PATENT DOCUMENTS

| | | | | |
|---|---|---|---|---|
| 5,960,106 | A * | 9/1999 | Tsuchiya et al. | 382/144 |
| 6,285,783 | B1 * | 9/2001 | Isomura et al. | 382/147 |
| 6,897,444 | B1 * | 5/2005 | Adler | 850/9 |
| 7,351,968 | B1 * | 4/2008 | Adler | 250/310 |
| 7,514,660 | B2 * | 4/2009 | Ikeda et al. | 250/201.2 |
| 7,554,082 | B2 * | 6/2009 | Motoki | 250/307 |
| 7,558,419 | B1 * | 7/2009 | Ye et al. | 382/144 |
| 7,796,801 | B2 * | 9/2010 | Kitamura et al. | 382/141 |
| 8,199,191 | B2 * | 6/2012 | Sato et al. | 348/80 |
| 2004/0126003 | A1 * | 7/2004 | Isomura et al. | 382/141 |
| 2007/0064994 | A1 * | 3/2007 | Oaki et al. | 382/144 |

FOREIGN PATENT DOCUMENTS

| | | |
|---|---|---|
| JP | 61-260235 | 11/1986 |
| JP | 10-332602 | 12/1998 |
| JP | 2001-291087 | 10/2001 |
| JP | 2001-357382 | 12/2001 |
| JP | 2003-303763 | 10/2003 |
| JP | 2005-205748 | 8/2005 |
| JP | 2006-132947 | 5/2006 |
| JP | 2007-71630 | 3/2007 |
| JP | 3965189 | 6/2007 |

(Continued)

OTHER PUBLICATIONS

Notice of Rejection issued by the Japanese Patent Office on Sep. 18, 2012, for Japanese Patent Application No. 2010-213574, and English-language translation thereof.

(Continued)

*Primary Examiner* — Andrae S Allison
(74) *Attorney, Agent, or Firm* — Finnegan, Henderson, Farabow, Garrett & Dunner, L.L.P.

(57) ABSTRACT

According to one embodiment, an alignment method includes setting a local area from an alignment target area, the local area being an execution target area of local alignment to be performed with precision equal to or higher than required alignment precision; performing the local alignment between a pattern image of an examination target and a reference pattern image of an examination reference, in the local area, to obtain a shift amount that is a result of local alignment; and shifting a whole of the reference pattern image by using the shift amount.

14 Claims, 10 Drawing Sheets

(56) References Cited

FOREIGN PATENT DOCUMENTS

| | | |
|---|---|---|
| JP | 2007-241356 | 9/2007 |
| JP | 2008-39712 | 2/2008 |
| JP | 2008-233343 | 10/2008 |
| JP | 2010-19667 | 1/2010 |
| JP | 2010-187347 | 8/2010 |
| JP | 2012-2674 | 1/2012 |

OTHER PUBLICATIONS

Notice of Rejection issued by the Japanese Patent Office on Jun. 4, 2013, for Japanese Patent Application No. 2010-213574, and English-language translation thereof.

* cited by examiner

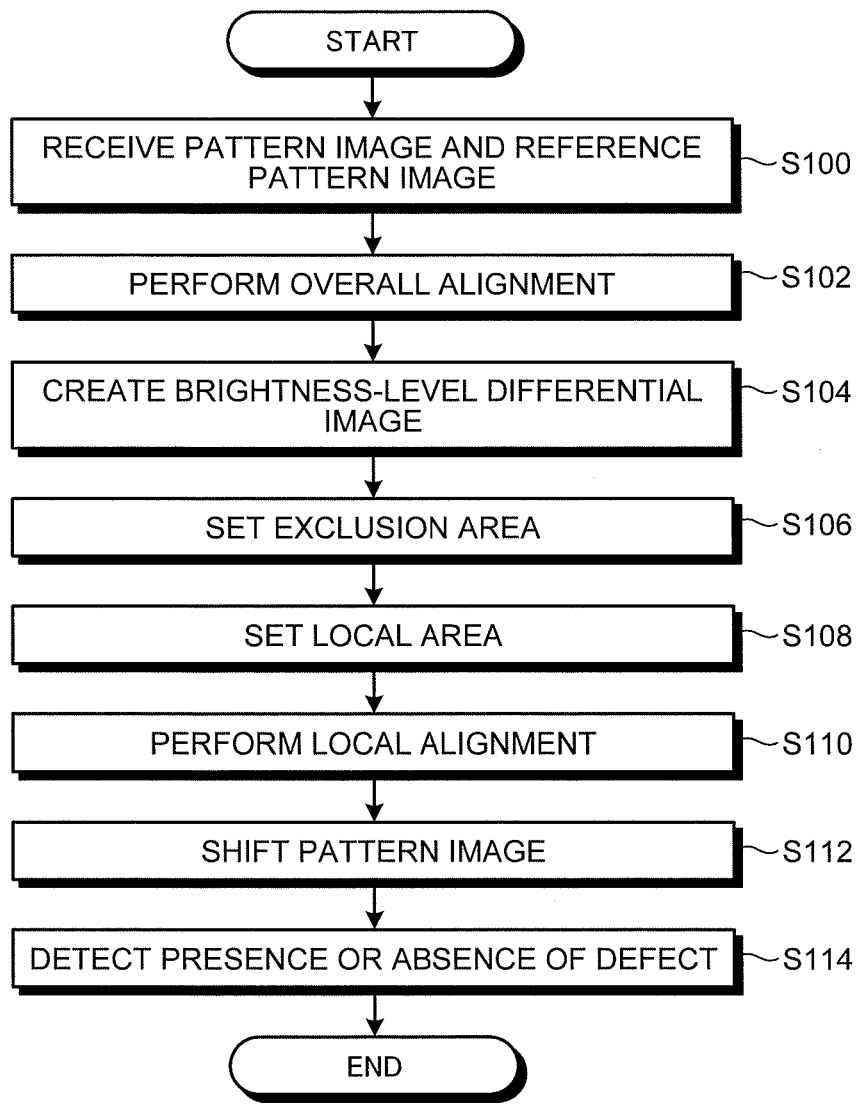

ALIGNMENT METHOD AND EXAMINATION APPARATUS

CROSS-REFERENCE TO RELATED APPLICATIONS

This application is based upon and claims the benefit of priority from Japanese Patent Application No. 2010-213574, filed on Sep. 24, 2010; the entire contents of which are incorporated herein by reference.

FIELD

Embodiments described herein relate generally to an alignment method and an examination apparatus.

BACKGROUND

Recently, as a Large Scale Integration (LSI) pattern size is getting finer, a pattern image that is formed on a photomask, such as a reticle, has been getting finer. As a result, the minimum size of a defect that needs to be detected, such as a defect on a pattern image, is getting finer, so that when comparing a pattern image and a reference pattern image to detect a defect on the pattern image, it needs to detect a deviation of pixel position between the pattern image and the reference pattern image, expansion-contraction and waviness of the pattern image, and a defect that may be buried in sensing noise.

For this reason, according to conventional technologies, as preprocessing of comparing a pattern image and a reference image, alignment on a per-pixel basis is performed, and then image corrections, such as resizing correction, expansion-contraction and waviness correction, and noise averaging processing, of the pattern image are performed.

However, according to the alignment on a per-pixel basis as described above according to the conventional technology, there is a possibility that the alignment ends in failure.

BRIEF DESCRIPTION OF THE DRAWINGS

FIG. 16 is a flowchart that depicts an example of alignment processing according to the embodiment.

DETAILED DESCRIPTION

According to one embodiment, an alignment method includes setting a local area from an alignment target area, the local area being an execution target area of local alignment to be performed with precision equal to or higher than required alignment precision; performing the local alignment between a pattern image of an examination target and a reference pattern image of an examination reference, in the local area, to obtain a shift amount that is a result of local alignment; and shifting a whole of the reference pattern image by using the shift amount.

Various embodiments will be described hereinafter with reference to the accompanying drawings. The following embodiments explain a case where an alignment method for a pattern image formed on a reticle is used in an examination apparatus that detects presence or absence of defect of a pattern image formed on a reticle, as an example; however, the embodiments are not limited to this.

Figure 1:
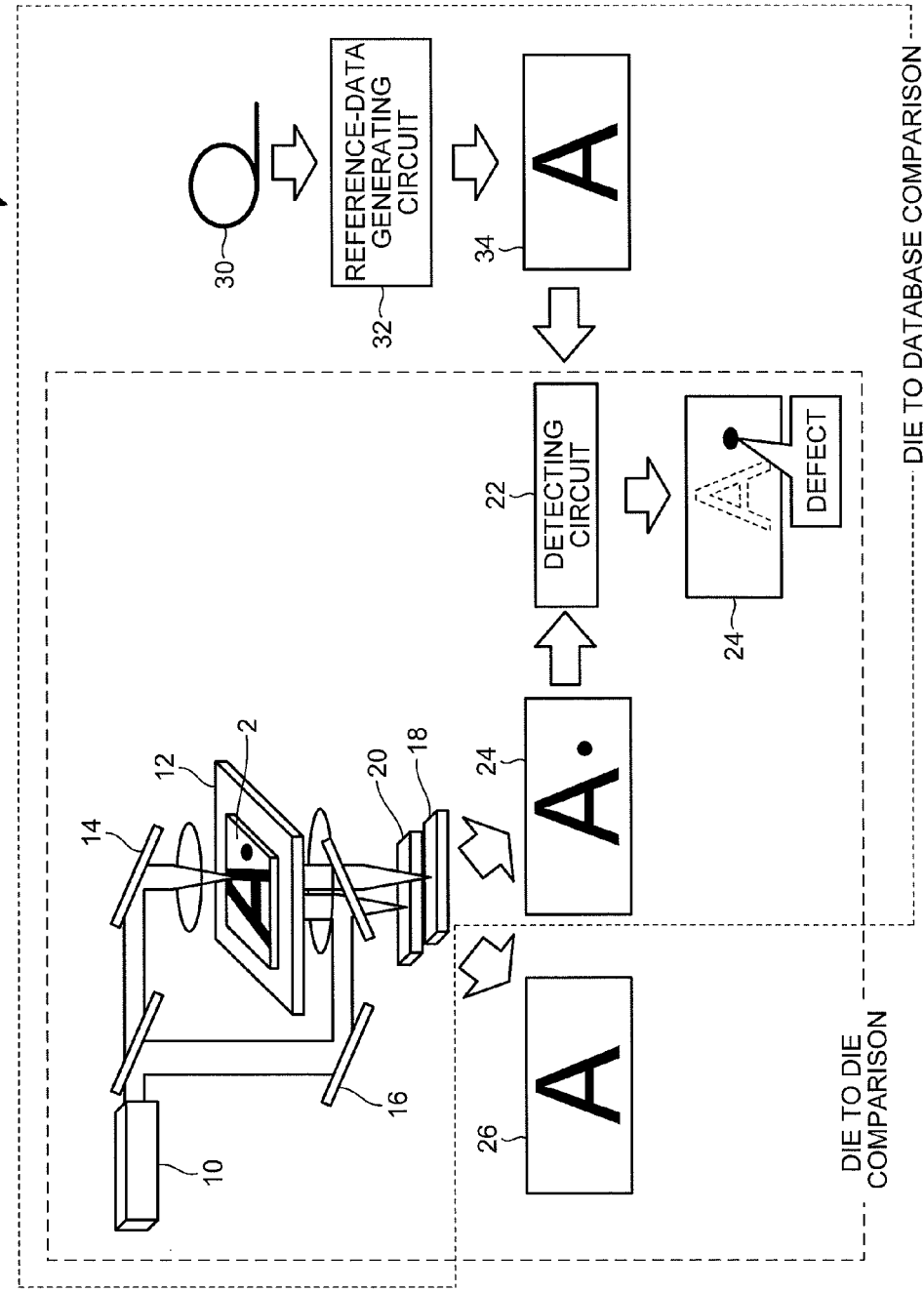
FIG. 1 is a configuration diagram that depicts an example of an examination apparatus according to an embodiment.

FIG. 1 is a configuration diagram that depicts an example of an examination apparatus 1 according to an embodiment. As shown in FIG. 1, the examination apparatus 1 includes a light source 10, a stage 12, a transmissive optical system 14, a reflective optical system 16, a transmitted light sensor 18, a reflected light sensor 20, and a detecting circuit 22.

The light source 10 generates light. The stage 12 places thereon a reticle 2. The stage 12 is driven by a not-shown driving system. The transmissive optical system 14 is configured such that the reticle 2 placed on the stage 12 transmits light from the light source 10. The reflective optical system 16 is configured such that reflected light of light emitted from the light source 10 onto the reticle 2 placed on the stage 12 can be detected. The transmissive optical system 14 and the reflective optical system 16 are constituted by, for example, a half mirror and a convex lens. The transmitted light sensor 18 detects transmitted light that is transmitted via the transmissive optical system 14, and acquires (records) sensor data 24 (for example, a pattern image) and sensor data 26 (for example, a reference pattern image) of respective two dies on the reticle 2. The reflected light sensor 20 detects reflected light via the reflective optical system 16, and acquires (records) the sensor data 24 (for example, a pattern image) and the sensor data 26 (for example, a reference pattern image) of respective two dies on the reticle 2.

Figure 2:
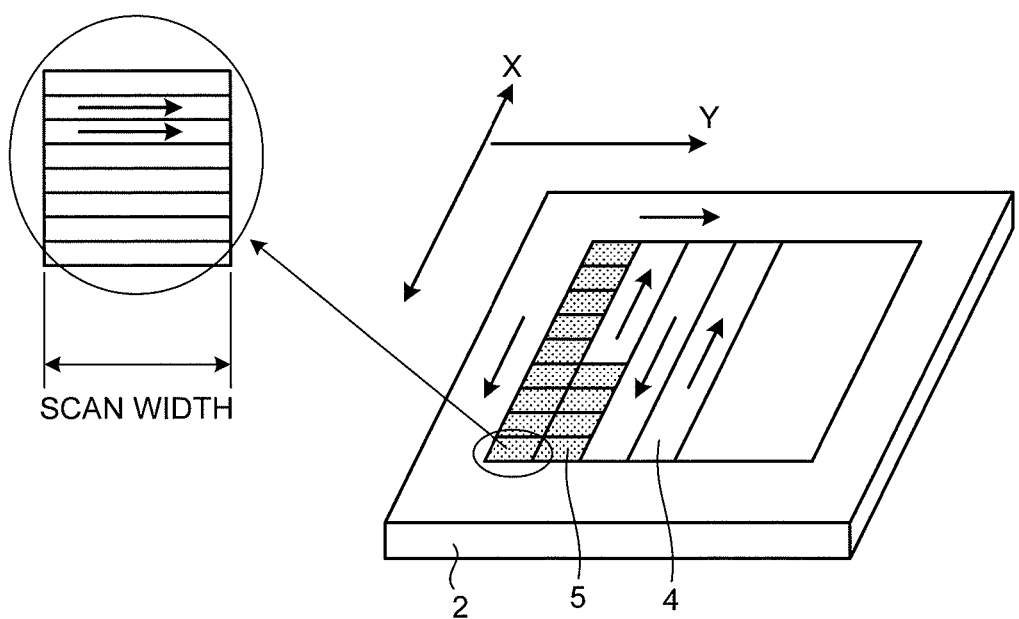
FIG. 2 is a schematic diagram for explaining an example of a method of acquiring a pattern image according to the embodiment.

FIG. 2 is a schematic diagram for explaining an example of a method of acquiring a pattern image according to the embodiment. As shown in FIG. 2, acquisition by the transmitted light sensor 18 of a pattern image formed on the reticle 2 is performed by scanning the reticle 2 with a line sensor (not shown in the figure). Here, a rectangular strip 4 that the reticle 2 is cut to long and narrow in an x-axis direction (the direction of one side of the reticle) shown in FIG. 2 is called a stripe, and then an image 5 that one stripe is finely cut to square further in a y-axis direction is called a sub-stripe. One stripe includes, for example, 2048 pixels in width; and one sub-stripe is assumed to include, for example, 2048×2048 pixels. Suppose here that one pixel is provided with 256-level gray scale. Moreover, it is assumed that an examination of presence or absence of defect on a pattern image by the examination apparatus 1 is to be performed for each sub-stripe. A similar method can be applied to acquisition of a reference pattern image.

Returning to FIG. 1, the detecting circuit 22 (an example of an examination apparatus) detects presence or absence of defect on a pattern image by comparing the pattern image with a reference pattern image. Comparison between a pattern image and a reference pattern image can be comparison between a die and a die (Die to Die comparison: DD comparison), or comparison between a die and database (Die to Database comparison: DB comparison). According to the comparison between a die and a die (DD comparison), the detecting circuit 22 detects presence or absence of defect in the sensor data 24 (pattern image) by comparing the sensor data 24 and the sensor data 26 recorded by the transmitted light sensor 18, or the sensor data 24 and the sensor data 26 recorded by the reflected light sensor 20. In contrast, according to the comparison between a die and database (DB comparison), the detecting circuit 22 detects presence or absence of defect in the sensor data 24 (pattern image) by comparing the sensor data 24 recorded by the transmitted light sensor 18 or the sensor data 24 recorded by the reflected light sensor 20, with design data 34 (reference pattern image) that is generated from a reference-data generating circuit 32 based on computer-aided design (CAD) data for LSI-designing 30.

Figure 3:
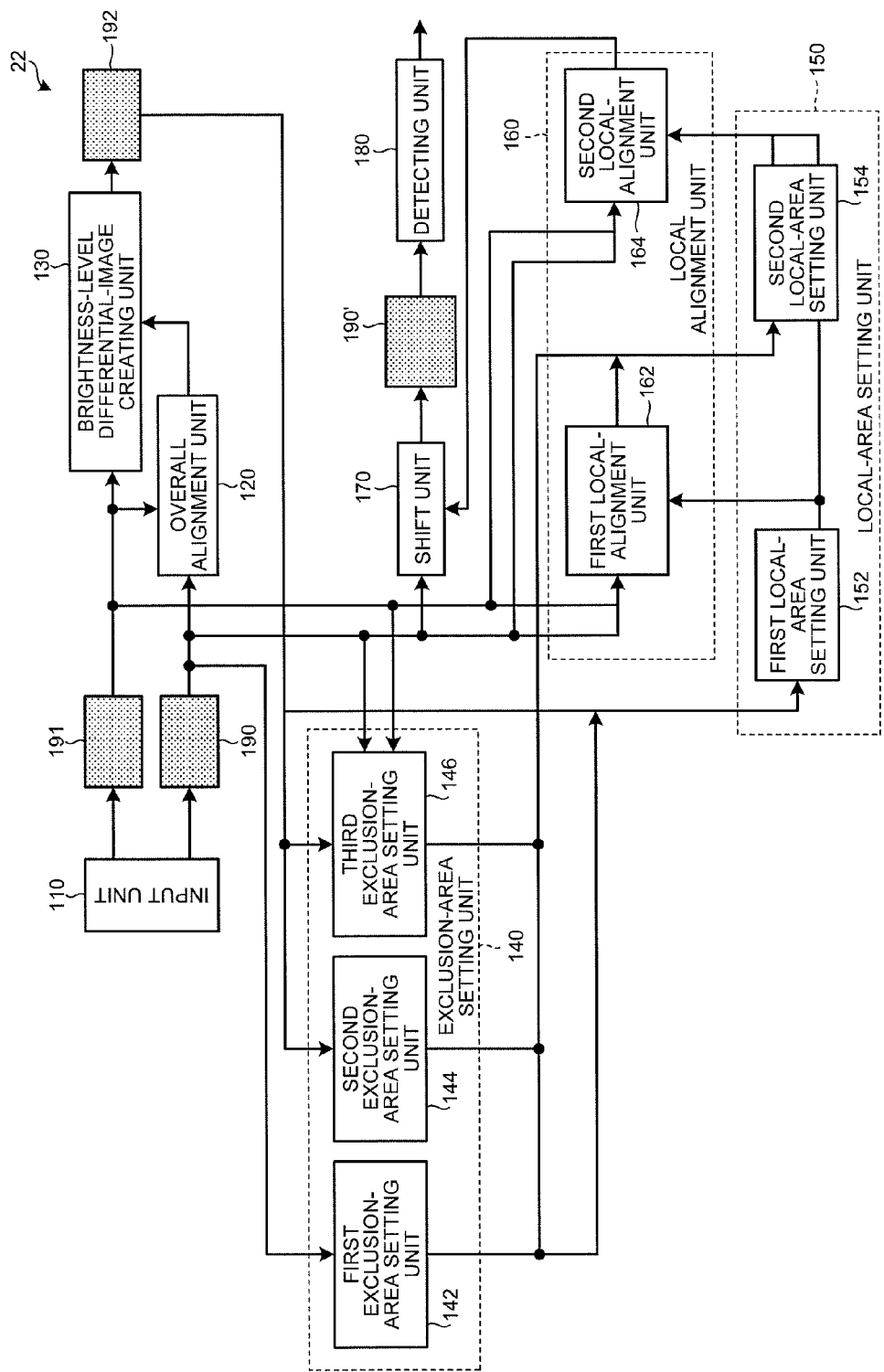
FIG. 3 is a configuration diagram that depicts an example of a detecting circuit according to the embodiment.

FIG. 3 is a configuration diagram that depicts an example of the detecting circuit 22 according to the embodiment. As shown in FIG. 3, the detecting circuit 22 includes an input unit 110, an overall alignment unit 120, a brightness-level differential-image creating unit 130, an exclusion-area setting unit 140, a local-area setting unit 150, a local alignment unit 160, a shift unit 170, and a detecting unit 180.

The input unit 110 receives a reference pattern image 190 that is an examination reference and a pattern image 191 that is an examination target, in units of sub-stripes explained in FIG. 2. It is assumed that the reference pattern image 190 and the pattern image 191 according to the embodiment are composed of a fine pattern equal to or higher than a sensor resolution, and a sufficient resolution has not been obtained. For this reason, comparison between the reference pattern image 190 and the pattern image 191 needs alignment finer than pixel order. According to the embodiment, it is assumed to achieve alignment higher than a sensor resolution by performing a pseudo shift of sub pixel order using bicubic interpolation (bicubic shift).

The overall alignment unit 120 performs overall alignment that is alignment targeting the whole effective area of each of the reference pattern image 190 and the pattern image 191 (2048×2048 pixels in the embodiment) received by the input unit 110. For example, the overall alignment unit 120 performs alignment processing by using a Sum of Square Differences (SSD) method of searching for a shift amount ($X_1$, $Y_1$) that makes a minimum sum of squares of brightness-level differentials of respective pixels of the reference pattern image 190 and the pattern image 191. Specifically, the overall alignment unit 120 performs the alignment processing by using the following Expressions (1) to (3).

$$M(X_1, Y_1) = \min(M(X, Y)) \quad (1)$$

$$M(X, Y) = \sum_y \sum_x \{I'_1(x, y) - I_2(x, y)\}^2 \quad (2)$$

$$I' = S(X, Y) \cdot I \quad (3)$$

In the expressions, I(x, y) denotes a brightness level value at coordinates (x, y) on an image. S(X, Y) denotes an image conversion using bicubic shift with a shift amount (X,Y), and I' denotes an image shifted from an image I. A shift amount is given as a discrete value that satisfies required alignment precision and a search area, assuming here that the shift amount falls within a range, −5<X<5, and −5<Y<5, per 1/16 pixel. Moreover, M(X, Y) denotes a matrix including 80×80 components that stores therein a sum of squares (SSD value) of brightness-level differentials with respect to each shift amount (X, Y), and the matrix is called a SSD map. An alignment method to be used for overall alignment is not limited to the SSD method, and other alignment algorithms can be used.

The brightness-level differential-image creating unit 130 shifts the reference pattern image 190 with a shift amount ($X_1$, $Y_1$) obtained by the overall alignment unit 120, and creates a brightness-level differential image 192 by using the reference pattern image 190 after the shift and the pattern image 191. The local-area setting unit 150, which will be described later, sets a local area to be an execution target of local alignment, by using the brightness-level differential image 192. The brightness-level differential-image creating unit 130 can be configured such that when the maximum level differential on the brightness-level differential image 192 is equal to or less than a default threshold, the brightness-level differential-image creating unit 130 determines that alignment has already succeeded, outputs a shift amount obtained by the overall alignment unit 120 to the shift unit 170 described later, and aborts processing that is described later.

The exclusion-area setting unit 140 sets an exclusion area to be excluded from an alignment target area, i.e., an exclusion area that is excluded (disallowed) from being set as a local area by the local-area setting unit 150 described later. The exclusion-area setting unit 140 includes a first exclusion-area setting unit 142, a second exclusion-area setting unit 144, and a third exclusion-area setting unit 146.

With respect to each pixel of the reference pattern image 190, when the maximum value of image brightness variations within a first predetermined range from the point of a pixel is equal to or less than a first threshold, the first exclusion-area setting unit 142 sets the point of the pixel to an exclusion area to be excluded from an alignment target area. For example, the first exclusion-area setting unit 142 sets the point of a pixel to an exclusion area, when a difference between the maximum brightness value and the minimum brightness value of image data within a range of ±10 pixels from the point of the pixel is equal to or less than 10, with respect to each pixel of the reference pattern image 190.

Figure 4:
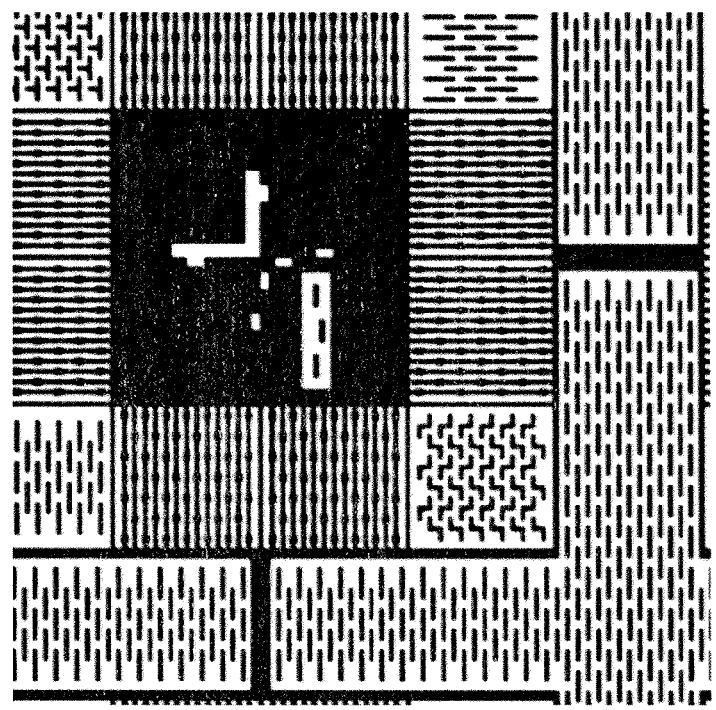
FIG. 4 is a schematic diagram that depicts an example of a reference pattern image according to the embodiment.
Figure 5:
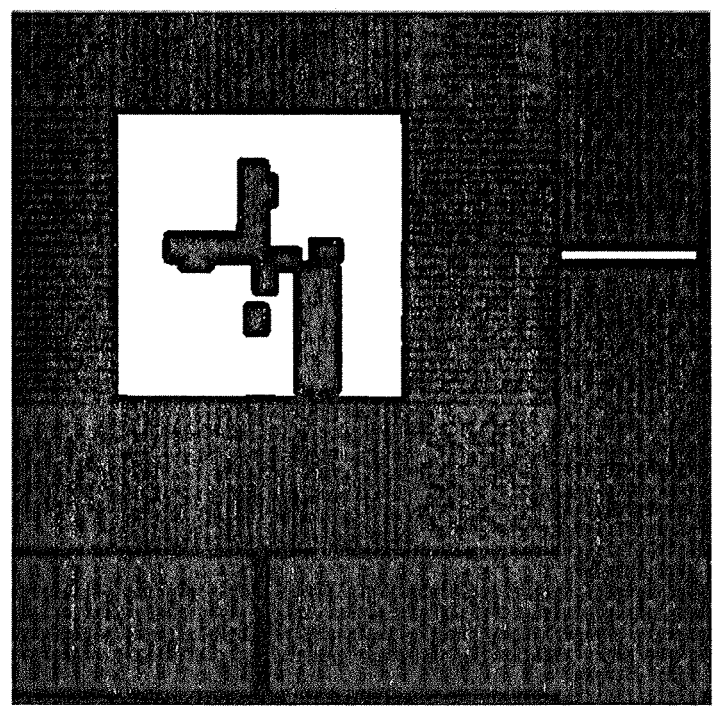
FIG. 5 is a schematic diagram that depicts an example of an exclusion area of a reference pattern image according to the embodiment.

FIG. 4 is a schematic diagram that depicts an example of the reference pattern image 190 according to the embodiment; and FIG. 5 is a schematic diagram that depicts an example of an exclusion area of the reference pattern image 190 according to the embodiment. According to the example shown in FIG. 5, the first exclusion-area setting unit 142 sets a solid white area to an exclusion area. Accordingly, this prevents the possibility that the local-area setting unit 150 described later sets an uncharacteristic area having little change in brightness level to a local area.

With respect to each pixel of the brightness-level differential image 192 created by the brightness-level differential-image creating unit 130, when a rate of the number of pixels having a brightness-level differential equal to or more than a second threshold to the number of pixels within a second predetermined range around the point of a pixel is equal to or more than a third threshold, the second exclusion-area setting unit 144 sets the point of the pixel as well as a predetermined area around the point of the pixel to an exclusion area to be excluded from an alignment target area. For example, with respect to each pixel of the brightness-level differential image 192, when the rate of the number of pixels each having a value equal to or more than 10 to the number of pixels within a predetermined pixel range around the point of the pixel is equal to or more than 0.2, the second exclusion-area setting unit 144 sets, as an exclusion area, the point of the pixel as well as an area of 10×10 pixels around the point of the pixel.

Figure 6:
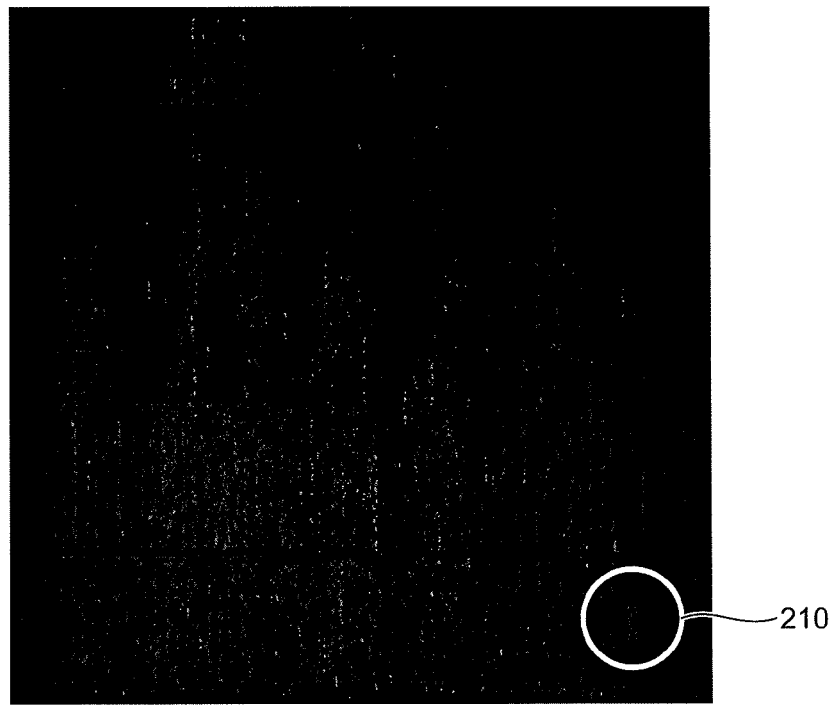
FIG. 6 is a schematic diagram that depicts an example of a brightness-level differential image according to the embodiment.
Figure 7:
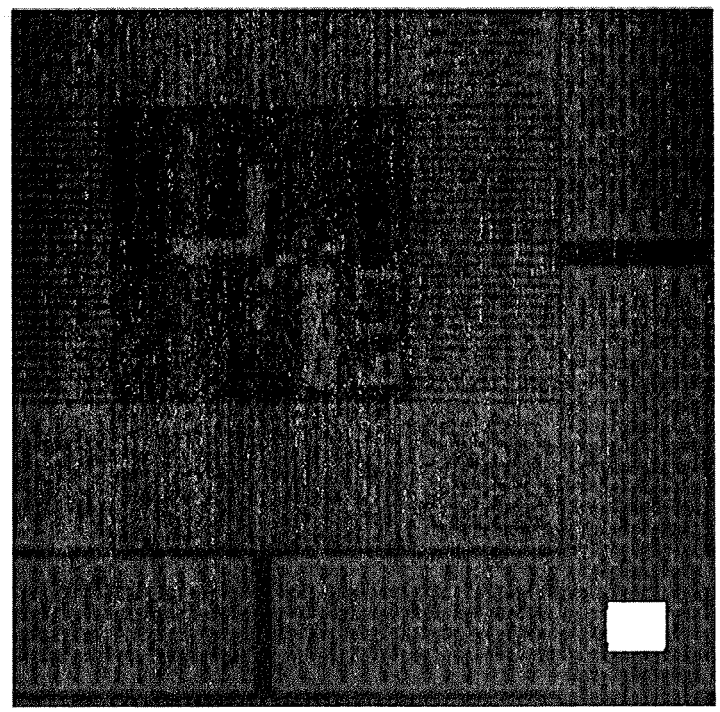
FIG. 7 is a schematic diagram that depicts an example of an exclusion area of a brightness-level differential image according to the embodiment.

FIG. 6 is a schematic diagram that depicts an example of the brightness-level differential image 192 according to the embodiment; and FIG. 7 is a schematic diagram that depicts an example of an exclusion area of the brightness-level differential image 192 according to the embodiment. According to the example shown in FIG. 7, the second exclusion-area setting unit 144 sets a solid white area (portion indicated by a circle 210 in the example shown in FIG. 6) to an exclusion area. Accordingly, the possibility of setting a local area onto a true defect by the local-area setting unit 150 described later is avoided.

The third exclusion-area setting unit 146 divides the brightness-level differential image 192 created by the brightness-level differential-image creating unit 130 into grid areas in a predetermined size. The third exclusion-area setting unit 146 then executes, in each grid area, SSD alignment weighted by weighting coefficients each corresponding to each pixel and corresponding to each value of a brightness-level differential at each pixel point in the divided grid area; obtains a shift amount that makes the minimum sum of squares of brightness-level differentials in the grid area weighted by the weighting coefficients, with respect to each grid area; and shifts the reference pattern image 190 by using the obtained shift amount. With respect to each pixel of a second brightness-level differential image obtained from the reference pattern image 190 after the shift and the pattern image 191, when a rate of the number of points, at which a difference in brightness-level differential from a corresponding point in the brightness-level differential image 192 is equal to or more than a fourth threshold, to the number of points in the second brightness-level differential image is equal to or more than a fifth threshold, the third exclusion-area setting unit 146 sets all of the points of the pixels in the grid area to an exclusion area to be excluded from an alignment target area.

For example, the third exclusion-area setting unit 146 divides the brightness-level differential image 192 into grid areas each of which includes 64 pixels lengthwise and crosswise. It is assumed here that the third exclusion-area setting unit 146 prepares a weighting coefficient D that is in proportion to a brightness-level differential d(x', y') at each pixel point (x', y') in the divided grid area. The third exclusion-area setting unit 146 then executes SSD alignment weighted by weighting coefficients that correspond to the respective pixels (hereinafter, referred to as weighted SSD) in the grid area, and obtains a shift amount (X', Y') that makes the minimum sum of squares of weighted brightness-level differentials, with respect to each grid. The third exclusion-area setting unit 146 shifts the whole of the reference pattern image 190 by using the obtained shift amount (X', Y'); and with respect to each pixel point on a brightness-level differential image dI' that is obtained from the reference pattern image 190 after the shift and the pattern image 191, when a rate of the number of points, at which a difference in brightness-level differential from a corresponding point in the brightness-level differential image 192 is equal to or more than 10, to the number of points in the whole of the brightness-level differential image dI' exceeds 0.3, the third exclusion-area setting unit 146 sets all of the points of the pixels in the grid area as an exclusion area.

Figure 8:
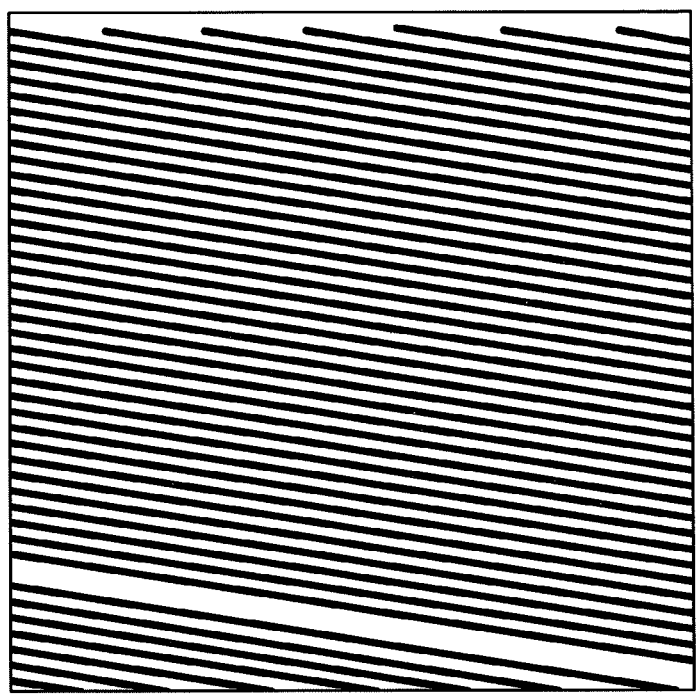
FIG. 8 is a schematic diagram that depicts an example of a pattern image according to the embodiment.
Figure 9:
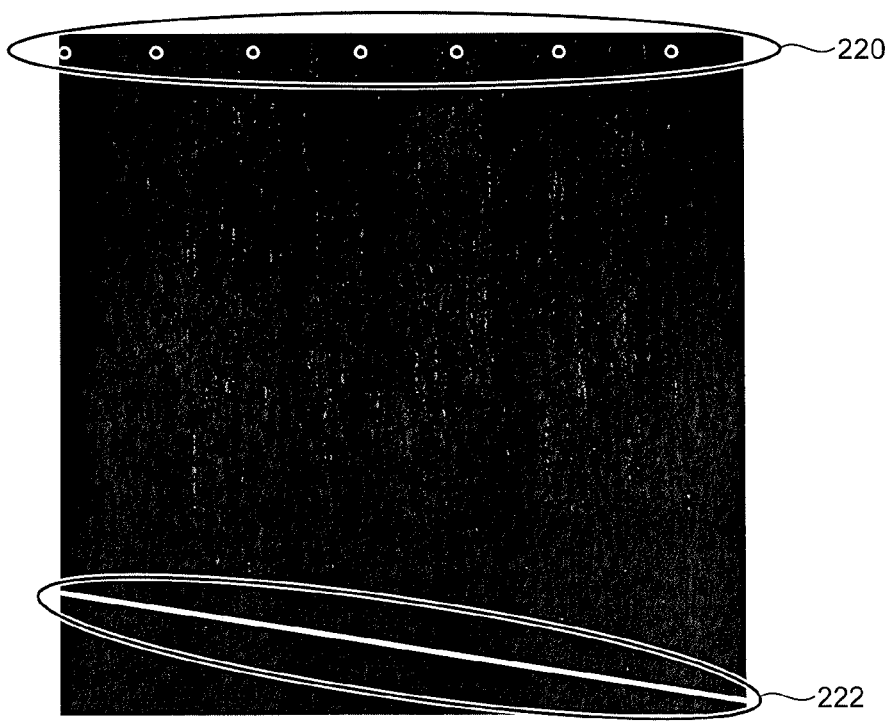
FIG. 9 is a schematic diagram that depicts an example of a brightness-level differential image according to the embodiment.
Figure 10:
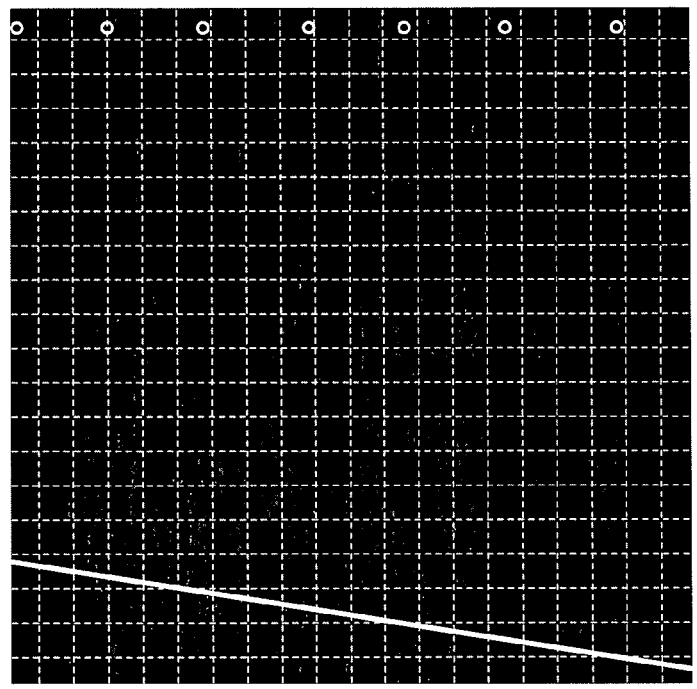
FIG. 10 is a schematic diagram that depicts an example of a brightness-level differential image divided into grid areas according to the embodiment.
Figure 11:
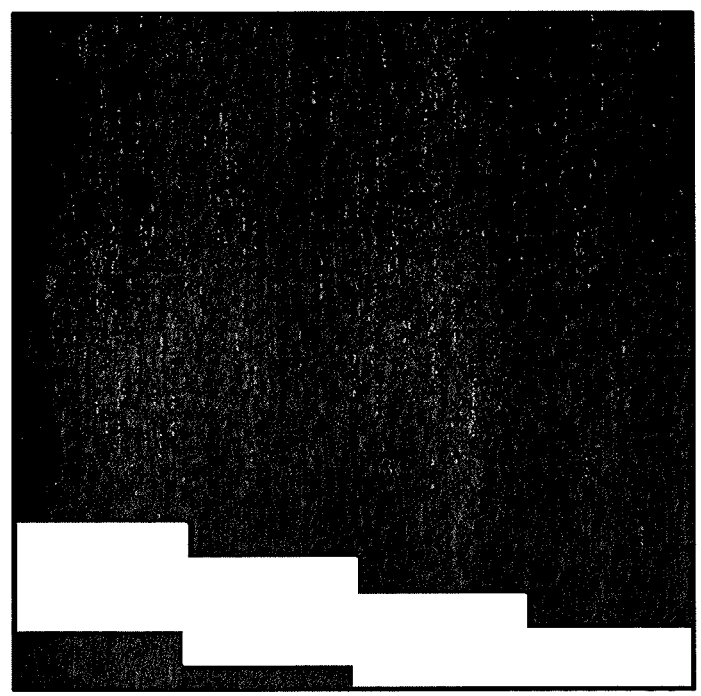
FIG. 11 is a schematic diagram that depicts an example of an exclusion area of a brightness-level differential image according to the embodiment.

FIG. 8 is a schematic diagram that depicts an example of the pattern image 191 according to the embodiment; FIG. 9 is a schematic diagram that depicts an example of the brightness-level differential image 192 according to the embodiment; FIG. 10 is a schematic diagram that depicts an example of the brightness-level differential image 192 divided into grid areas according to the embodiment; and FIG. 11 is a schematic diagram that depicts an example of an exclusion area of the brightness-level differential image 192 according to the embodiment. According to the example shown in FIG. 11, the third exclusion-area setting unit 146 sets a solid white area as an exclusion area. It should be noted that, in the example shown in FIG. 11, a pseudo defect 220 by error of the overall alignment shown in FIG. 9 is not set as an exclusion area, and only an actual defect 222 shown in FIG. 9 is set as an exclusion area. Accordingly, while avoiding setting a local area onto a true defect by the local-area setting unit 150 described later, it is allowed to select a local area onto the pseudo defect.

The local-area setting unit 150 sets, from an alignment target area, a local area that is an execution target area of local alignment to be performed with precision equal to or higher than required alignment precision of a pattern image. Specifically, the local-area setting unit 150 sets a plurality of local areas with predetermined intervals in order from a point with a large brightness-level differential, from among areas excluding an exclusion area set by the exclusion-area setting unit 140 in the area of the brightness-level differential image 192 created by the brightness-level differential-image creating unit 130. For example, the local-area setting unit 150 sets one point with the largest brightness-level differential on the brightness-level differential image 192 created by the brightness-level differential-image creating unit 130, and sets the point as a local area point 1. Similarly, the local-area setting unit 150 sets another one point with the second largest brightness-level differential next to the local area point 1 at a distance of 100 pixels or farther from the local area point 1, and sets said another one point as a local area point 2. Similarly, the local-area setting unit 150 sets still another one point with the third largest brightness-level differential next to the local area point 2 at a distance of 100 pixels or farther from the local area points 1 and 2, and sets said still another one point as a local area point 3.

According to the embodiment, the local-area setting unit 150 is assumed to set local area points up to three, however, not limited to this, any number of local area points can be set. The above processing is repeated up to a set number of local area points. Moreover, according to the embodiment, a local area is expressed by a square area around a centered local area point, and assumed here to have a size of 21×21 pixels. However, if the area dimension of exclusion areas is large, and an area available for setting therein a local area is narrow; the local-area setting unit 150 sets local area points by changing intervals between the local area points to smaller than 100 pixels.

The local-area setting unit 150 includes a first local-area setting unit 152, and a second local-area setting unit 154.

However, not limited to this, the number of local-area setting units can be one, or three or more. The first local-area setting unit 152 is configured to perform local area setting of the first time, and the second local-area setting unit 154 is configured to perform local area setting of the second time; and local-area setting methods are substantially similar.

The local alignment unit 160 performs local alignment between the reference pattern image 190 and the pattern image 191 with respect to each of the local areas set by the local-area setting unit 150, and obtains a shift amount as a result of the local alignment. Specifically, the local alignment unit 160 quantifies local alignment characteristics of each of a plurality of local areas set by the local-area setting unit 150, selects a local area of an execution target of local alignment, and performs the local alignment between the reference pattern image 190 and the pattern image 191 in the selected local area.

Figure 12:
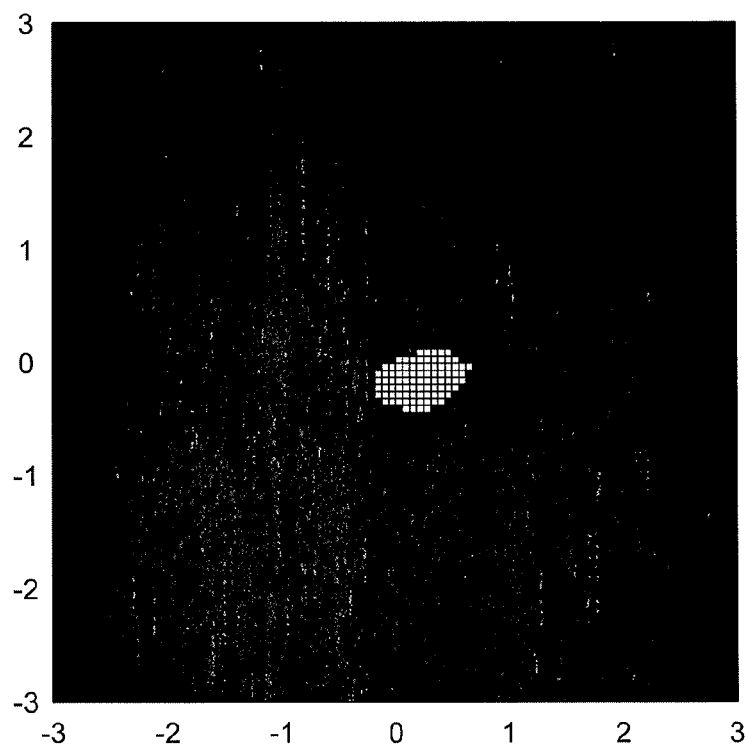
FIG. 12 is a schematic diagram that depicts an example of a binarized Sum of Square Differences (SSD) map according to the embodiment.
Figure 13:
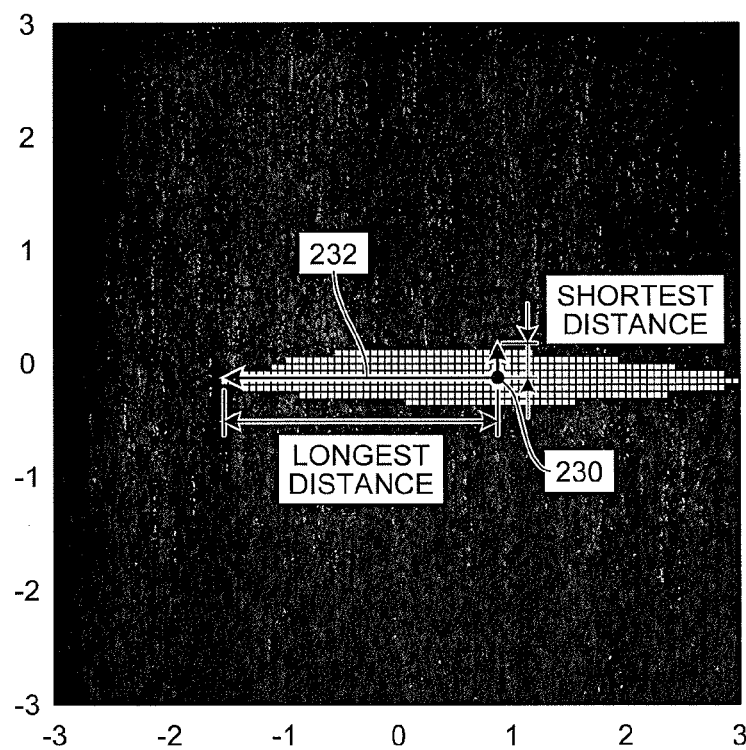
FIG. 13 is a schematic diagram that depicts an example of a binarized SSD map according to the embodiment.
Figure 14:
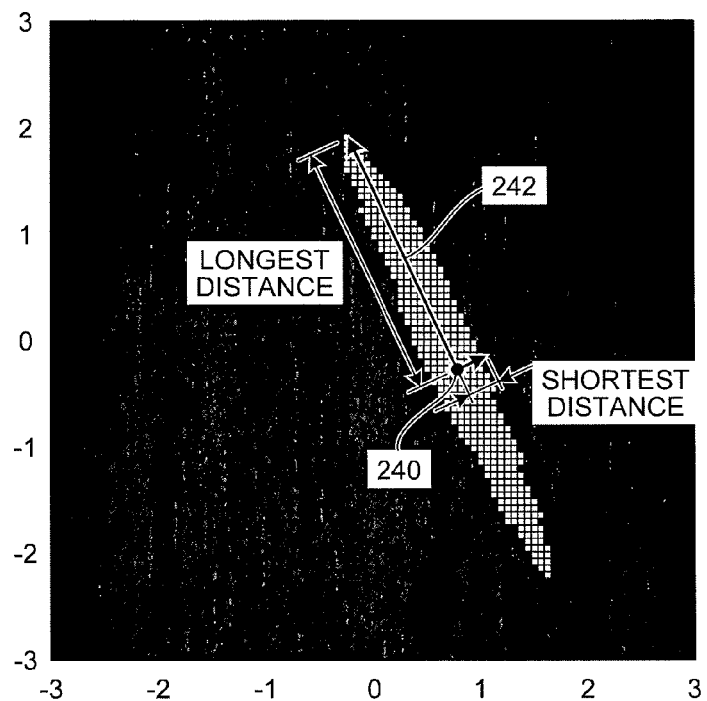
FIG. 14 is a schematic diagram that depicts an example of a binarized SSD map according to the embodiment.

For example, the local alignment unit 160 executes local alignment limited to a local area with respect to each of the local areas selected by the local-area setting unit 150, and creates an SSD map $M_p(X, Y)$ of each of the local areas that a list of sums of squares of brightness-level differentials at the moment of a virtual shift obtained by the local alignment is arranged and graphed in accordance with the shift direction and the shift amount (hereinafter, referred to as a local SSD map). Moreover, the local alignment unit 160 creates a normalized SSD map $M_n(X, Y)$ that all elements in the local SSD map are divided by the minimum value in the local SSD map, with respect to each of the created local SSD maps. Furthermore, the local alignment unit 160 creates a binary map $M_b(X, Y)$ that each element having a value of three or more and each element having a value less than three in the normalized SSD map are binarized to 0 and 1, respectively (hereinafter, referred to as a binarized SSD map), with respect to each of the created normalized SSD maps. FIGS. 12 to 14 are schematic diagrams that depict examples of a binarized Sum of Square Differences (SSD) map according to the embodiment. Specifically, the local alignment unit 160 creates a local SSD map by using Expression (4), creates a normalized SSD map by using Expressions (5) and (6), and creates a binarized SSD map by using Expression (7). Here, the local SSD map, the normalized SSD map, and the binarized SSD map correspond to quantified local-alignment characteristics.

$$M_p(X, Y) = \sum_{y=y_i-d}^{y_i+d} \sum_{x=x_i-d}^{x_i+d} \{I'_1(x, y) - I_2(x, y)\}^2 \quad (4)$$

$$M_n(X, Y) = \frac{M_p(X, Y)}{M_p(X_{min}, Y_{min})} \quad (5)$$

$$M_p(X_{min}, Y_{min}) = \min(M_p(X, Y)) \quad (6)$$

$$M_b(X, Y) = \begin{cases} 1 & (M_n(X, Y) \geq U) \\ 0 & (M_n(X, Y) < U) \end{cases} \quad (7)$$

In the above expression, $(x_i, y_i)$ denotes a local area point selected at the i-th time, d denotes a half size of the local area, and U denotes a threshold for binarization. According to the embodiment, d=10, and U=3.

Moreover, by using characteristic areas formed by the binarized SSD map as an index, the local alignment unit 160 selects a first local area that includes a first characteristic area to be a reference from among characteristic areas included in respective local areas, and selects, as a local area of an execution target of local alignment, a local area in a higher order of combinations by which a concealment rate of the first characteristic area is made large to the OR dimension that is formed between the first characteristic area included in the selected first local area and a second characteristic area included in a second local area that is another local area. Here, the first local area is such that the maximum brightness-level differential between the reference pattern image 190 and the pattern image 191 on which a local shift is performed with a shift amount that is the minimum value on the local SSD map is equal to or less than a sixth threshold, and one of the OR dimensions with the binarized SSD map of the second local area is not 0, and the area dimension of the area on the binarized SSD map is the smallest.

For example, by using $(X_{min}, Y_{min})$ that satisfies $M_p(X_{min}, Y_{min}) = \min M_p(X, Y)$, the local alignment unit 160 selects, as the first local area, an area that one of the OR map dimension $S_{sum}$ with the binarized SSD map of a local area other than its own area is not 0, and an area dimension S on the binarized SSD map is the smallest, from among a local image that a local area on the reference pattern image 190 corresponding to the local SSD map is shifted, and a local image that the maximum value on a local brightness-level differential image with the pattern image 191 is equal to or less than 20. For example, when the binarized SSD maps shown in FIGS. 12 to 14 are present, the local alignment unit 160 selects the binarized SSD map shown in FIG. 12, which has the smallest area dimension S on the binarized SSD map, as the first local area. Moreover, for example, when the binarized SSD maps shown in FIGS. 13 and 14 are present, the local alignment unit 160 selects the binarized SSD map shown in FIG. 13, which has the smallest area dimension S on the binarized SSD map, as the first local area. S and $S_{sum}$ are expressed by Expression (8) to (10), respectively.

$$S = \text{num}(M_b) \quad (8)$$

$$S_{sum\ ij} = \text{num}(M_{b\_sum\ ij}) \quad (9)$$

$$M_{b\_sum\ ij}(X, Y) = M_{bi}(X, Y) \hat{} M_{bj}(X, Y) \quad (10)$$

In the above expressions, $S_{sum\ ij}$ denotes the area dimension of two local areas i and j; $\text{num}(M_b)$ denotes the number of the values of 1 in the binarized SSD map $M_b$; and $M_{bi} \hat{} M_{bj}$ denotes the OR of respective elements of the two binarized SSD maps. For example, when the values of $M_{bi}$ and $M_{bj}$ are 1, the value of $M_{b\_sum\ ij}$ is also 1; and when at least one of the values of $M_{bi}$ and $M_{bj}$ is 0, the value of $M_{b\_sum\ ij}$ is 0.

Here, an aggregation of $(X, Y)$ that satisfies $M_b(X, Y)=1$ on the binarized SSD map is called "area". Furthermore, as shown in FIGS. 13 and 14, in the areas on the binarized SSD maps, a distance from each of local SSD-map minimal points 230 and 240 to an area end point to which the distance is the longest is a longest distance, and a distance from each of the minimal points 230 and 240 to an area end point to which the distance is the shortest is a shortest distance. The local alignment unit 160 categorizes an area of which ratio between its longest distance and its shortest distance is three or higher as "a long-and-narrow area", and the longest distance direction of the long-and-narrow area is called an "attitude vector" of the area (an attitude vector 232 in the example shown in FIG. 13, and an attitude vector 242 in the example shown in FIG. 14).

Figure 15:
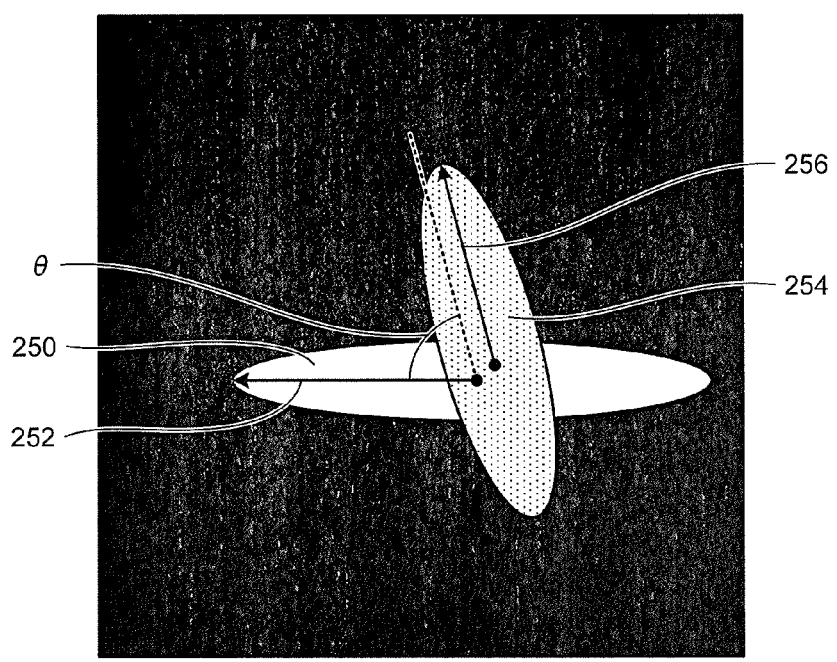
FIG. 15 is a schematic diagram that depicts an example of a first characteristic area and a second characteristic area according to the embodiment.

Moreover, as shown in FIG. 15, when a first characteristic area 250 is a long-and-narrow area, the local alignment unit 160 sets, as a second characteristic area 254, a characteristic area which has 10 or more degrees of an interior angel θ of the attitude vector and at which a rate δ of hiding the first characteristic area 250 is the largest, and sets, as a second local area, a local area that includes the second characteristic area 254. In other words, the second local area includes the second characteristic area that is not in parallel with the first characteristic area. According to the example shown in FIG. 15, the attitude vector of the first characteristic area 250 is a first attitude vector 252, and the attitude vector of the second characteristic area 254 is a second attitude vector 256.

Here, θ and δ are expressed by Expressions (11) and (12), respectively. When θ>90 degrees, an angle of θ-90 degrees is used in Expression (11).

$$\theta_{ij} = \cos^{-1} \frac{\vec{a}_i \cdot \vec{a}_j}{|\vec{a}_i||\vec{a}_j|} \quad (11)$$

$$\delta_{ij} = \frac{S_{sum\_ij}}{S_i} \quad (12)$$

In the above expressions, $\delta_{ij}$ denotes the concealment rate of the first characteristic area i to the second characteristic area j. When using a plurality of second local areas, a required number of rates are selected from a higher order of the concealment rates of the first characteristic area. The number of the second local areas is assumed one in the embodiment.

Moreover, the local alignment unit 160 creates a composite local SSD map $M_{p\_sum}$ by summing up a first local SSD map and a second local SSD map. $M_{p\_sum}$ is expressed by Expression (13).

$$M_{p\_sum}(X,Y) = M_{p1}(X,Y) + M_{p2}(X,Y) \quad (13)$$

In the above expression, $M_{p1}$ denotes a local SSD map of the first local area, and $M_{p2}$ denotes a local SSD map of the second local area. When there is a plurality of second local areas, all of them are summed up. The local alignment unit 160 then obtains a shift amount $(X_p, Y_p)$ that satisfies $M_{p\_sum}(X_p, Y_p) = \min(M_{p\_sum}(X,Y))$, with respect to $M_{p\_sum}$. This means that SSD is performed by using only the inside of the local areas on the reference pattern image 190.

The local alignment unit 160 includes a first local-alignment unit 162, and a second local-alignment unit 164. However, not limited to this, the number of local alignment units can be one, or three or more. The first local-alignment unit 162 is configured to perform local alignment of the first time, and the second local-alignment unit 164 is configured to perform local alignment of the second time; and local-area setting methods are substantially similar.

When the first local-alignment unit 162 performs the processing described above, the first local-alignment unit 162 shifts (applies) the whole of the reference pattern image 190 with the obtained shift amount $(X_p, Y_p)$, and outputs it to the second local-area setting unit 154. The second local-area setting unit 154 creates a brightness-level differential image between the reference pattern image 190 after the shift and the pattern image 191, and again determines a local area through the procedure similar to the method described above. In the second local-area setting unit 154, to distinguish a local area of a setting target from a local area that has been previously set, the local area of a setting target is called a secondary local area, and the previously-set local area is called a primary local area. Similarly, a first local area of a selection target is called a secondary first local area, and a first characteristic area of a selection target is called a secondary first characteristic area.

The second local-alignment unit 164 creates a composite local SSD map $M_{p\_sum2}$ that the primary local area and the secondary local area are all summed up. $M_{p\_sum2}$ is expressed by Expression (14). $M_{p1\_1}$ denotes the primary first local area; $M_{p2\_1}$ denotes the primary second local area; $M_{p1\_2}$ denotes the secondary first local area; and $M_{p2\_2}$ denotes the secondary second local area. Moreover, when there is a plurality of second local areas, the second local-alignment unit 164 also sums up all of them. The second local-alignment unit 164 obtains a shift amount $(X_{p2}, Y_{p2})$ that satisfies $M_{p\_sum2}(X_{p2}, Y_{p2}) = \min(M_{p\_sum2}(X,Y))$, with respect to $M_{p\_sum2}$.

$$M_{p\_sum2}(X,Y) = M_{p1\_1}(X,Y) + M_{p2\_1}(X,Y) + M_{p1\_2}(X,Y) + M_{p2\_2}(X,Y) \quad (14)$$

The shift unit 170 shifts the whole of the reference pattern image 190 by using a shift amount $(X_{p2}, Y_{p2})$ obtained by the local alignment unit 160, and creates a reference pattern image 190' after the shift.

The detecting unit 180 outputs the reference pattern image 190' shifted by the shift unit 170 as an alignment result image. The detecting unit 180 takes, for example, a differential image, by using the reference pattern image 190' after the shift and the pattern image 191, and performs detection so as to extract a part having a relatively large brightness-level differential in the differential image as a defective part.

FIG. 16 is a flowchart that depicts an example of a flow of a procedure of alignment processing (detecting processing) performed by the detecting circuit 22 according to the embodiment.

To begin with, the input unit 110 receives the reference pattern image 190 and the pattern image 191 that is the examination target, in units of sub-stripes explained in FIG. 2 (Step S100).

Subsequently, the overall alignment unit 120 performs overall alignment of the reference pattern image 190 and the pattern image 191 received by the input unit 110 (Step S102).

Subsequently, the brightness-level differential-image creating unit 130 shifts the reference pattern image 190 with a shift amount $(X_1, Y_1)$ obtained by the overall alignment unit 120, and creates the brightness-level differential image 192 by using the reference pattern image 190 after the shift and the pattern image 191 (Step S104).

Subsequently, the exclusion-area setting unit 140 sets an exclusion area to be excluded from an alignment target area, i.e., an exclusion area that is excluded (disallowed) from being set as a local area by the local-area setting unit 150 described later (Step S106).

Subsequently, the local-area setting unit 150 sets, from an alignment target area, a local area that is an execution target area of local alignment to be performed with precision equal to or higher than required alignment precision of a pattern image (Step S108).

Subsequently, the local alignment unit 160 performs local alignment between the reference pattern image 190 and the pattern image 191 with respect to each of the local areas set by the local-area setting unit 150, and obtains a shift amount as a result of the local alignment (Step S110).

Subsequently, the shift unit 170 shifts the whole of the reference pattern image 190 by using the shift amount obtained by the local alignment unit 160, and creates the reference pattern image 190' after the shift (Step S112).

Subsequently, the detecting unit 180 takes, for example, a differential image, by using the reference pattern image 190' after the shift shifted by the shift unit 170 and the pattern image 191, and performs detection so as to extract a part having a relatively large brightness-level differential in the differential image as a defective part (Step S114).

As described above, according to the embodiment, by performing alignment limited to a local area, the volume of calculation can be significantly reduced, accordingly, alignment calculation with high precision with a heavy load can be executed all over the search shift areas. Furthermore, according to the embodiment, to reduce load, it does not need to obtain an alignment shift amount by improving SSD precision while narrowing a search area stepwise, so that minimum solutions like local minima can be avoided.

Moreover, according to the embodiment, by performing excluding processing and selecting processing of local area selection, it can avoid including an actual defect part into a local area, and can avoid selecting, as a local area, a part with little characteristic information for alignment, such as a repeated pattern or an uncharacteristic area having little change in brightness level. Therefore, according to the embodiment, it can avoid burying characteristic information, and alignment can be successfully performed more robustly even on a special line pattern that is conventionally difficult to cope with.

Furthermore, as described in the embodiment, by performing local alignment a plurality of number of times, even when a local area having high directivity of functioning only effective on a particular directional component is selected at the first-time local alignment, selecting a local area at the second time from a brightness-level differential image obtained in consequence enables a positive selection of a local area appropriate for suppressing a directional component that is not able to be aligned at the first time, i.e., the directional component at which alignment is weak in the first-time local area. In such case, during the second alignment, it is preferable to use the primary local area simultaneously in addition to the secondary local area. By repeatedly executing calculation a plurality of number of times, its suppression can be more effective.

As described above, the embodiment can improve alignment precision.

Moreover, it can be configured such that the detecting unit compares a result of overall alignment and a result of local alignment, determines which result is a more certain alignment result, for example, which result is applied to an image shift after which a total sum of brightness-level differentials is smaller, and finally outputs the one that is more certain.

The parameter numerical values used in the embodiment are merely by way of an example. The numerical values vary depending on the resolution of a sensor used in the examination apparatus, sensitivity of the sensor, the intensity of a light source, a pattern size of an examination target, and the processing capacity of a computer, therefore, the values are not limited.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An alignment method comprising:
    setting, with respect to each pixel on a reference pattern image of an examination reference, when a maximum value of image brightness variations within a first predetermined range from a point of a pixel is equal to or less than a first threshold, the point of the pixel to an exclusion area;
    setting a local area from among areas excluding the exclusion area in an alignment target area, the local area being an execution target area of local alignment;
    performing the local alignment between a pattern image of an examination target and the reference pattern image in the local area, to obtain a shift amount that is a result of local alignment; and
    shifting a whole of the reference pattern image by using the shift amount.

2. The alignment method according to claim 1, further comprising:
    performing overall alignment between the pattern image and the reference pattern image;
    generating a brightness-level differential image between the pattern image and the reference pattern image after the overall alignment; and
    setting, with respect to each pixel on the brightness-level differential image, when a rate of number of pixels having a brightness-level differential equal to or more than a second threshold to number of pixels within a second predetermined range around a point of a pixel is equal to or more than a third threshold, the point of the pixel and a predetermined area around the point of the pixel to the exclusion area.

3. The alignment method according to claim 2, wherein
    the alignment target area is an area of the brightness-level differential image, and
    the setting the local area includes setting, as the local area, an area that is based on a point having a largest brightness-level differential from among areas excluding the exclusion area in the area of the brightness-level differential image.

4. The alignment method according to claim 3, wherein
    the setting the local area includes setting a plurality of local areas with predetermined intervals in order from a point with a large brightness-level differential, from among areas excluding the exclusion area in the area of the brightness-level differential image, and
    the performing the local alignment includes quantifying local alignment characteristics of each of the local areas, selecting a local area of an execution target of local alignment, and performing the local alignment between the pattern image and the reference pattern image in selected local area.

5. The alignment method according to claim 4, wherein
    the local alignment characteristics quantified are a local SSD map that a list of sums of squares of brightness-level differentials at a moment of a virtual shift obtained by local alignment is arranged and graphed in accordance with a shift direction and a shift amount, a normalized SSD map that the local SSD map is normalized, and a binarized SSD map that the normalized SSD map is binarized, and
    the setting the local area includes selecting a first local area that includes a first characteristic area to be a reference from among characteristic areas included in respective local areas by using characteristic areas formed by the binarized SSD map as an index, and selecting, as a local area of an execution target of local alignment, a local area in a higher order of combinations by which a concealment rate of the first characteristic area is made large to the OR dimension that is formed between the first characteristic area included in selected first local area and a second characteristic area included in a second local area that is another local area.

6. The alignment method according to claim 5, wherein the first local area is such that
    a maximum value of brightness-level differentials between the pattern image and the reference pattern image on which a local shift is performed with a shift amount of a minimum value on the local SSD map is equal to or less than a sixth threshold, one of OR dimensions with the binarized SSD map of the second local area is not 0, and an area dimension of area on the binarized SSD map is smallest.

7. The alignment method according to claim 5, wherein the second local area includes a second characteristic area that is not parallel with the first characteristic area.

8. The alignment method according to claim 1, further comprising:

performing overall alignment between the pattern image and the reference pattern image;

generating a brightness-level differential image between the pattern image and the reference pattern image after the overall alignment;

dividing the brightness-level differential image into grid areas in a predetermined size;

executing, in the grid area, Sum of Square Differences (SSD) alignment weighted by weighting coefficients each corresponding to each pixel and corresponding to each value of a brightness-level differential at each pixel point in divided grid area;

obtaining a shift amount that makes a minimum sum of squares of brightness-level differentials in an area weighted by the weighting coefficients;

shifting the reference pattern image by using obtained shift amount; and setting, with respect to each pixel of a second brightness-level differential image obtained from the reference pattern image after the shift and the pattern image, when a rate of number of points, at which a difference in brightness-level differential from a corresponding point in the brightness-level differential image is equal to or more than a fourth threshold, to number of points in the second brightness-level differential image is equal to or more than a fifth threshold, all points of pixels in a grid area to the exclusion area.

9. The alignment method according to claim 8, wherein the alignment target area is an area of the brightness-level differential image, and the setting the local area includes setting, as the local area, an area that is based on a point having a largest brightness-level differential from among areas excluding the exclusion area in the area of the brightness-level differential image.

10. The alignment method according to claim 9, wherein the setting the local area includes setting a plurality of local areas with predetermined intervals in order from a point with a large brightness-level differential, from among areas excluding the exclusion area in the area of the brightness-level differential image, and the performing the local alignment includes quantifying local alignment characteristics of each of the local areas, selecting a local area of an execution target of local alignment, and performing the local alignment between the pattern image and the reference pattern image in selected local area.

11. The alignment method according to claim 10, wherein the local alignment characteristics quantified are a local SSD map that a list of sums of squares of brightness-level differentials at a moment of a virtual shift obtained by local alignment is arranged and graphed in accordance with a shift direction and a shift amount, a normalized SSD map that the local SSD map is normalized, and a binarized SSD map that the normalized SSD map is binarized, and the setting the local area includes selecting a first local area that includes a first characteristic area to be a reference from among characteristic areas included in respective local areas by using characteristic areas formed by the binarized SSD map as an index, and selecting, as a local area of an execution target of local alignment, a local area in a higher order of combinations by which a concealment rate of the first characteristic area is made large to the OR dimension that is formed between the first characteristic area included in selected first local area and a second characteristic area included in a second local area that is another local area.

12. The alignment method according to claim 11, wherein the first local area is such that a maximum value of brightness-level differentials between the pattern image and the reference pattern image on which a local shift is performed with a shift amount of a minimum value on the local SSD map is equal to or less than a sixth threshold, one of OR dimensions with the binarized SSD map of the second local area is not 0, and an area dimension of area on the binarized SSD map is smallest.

13. The alignment method according to claim 11, wherein the second local area includes a second characteristic area that is not parallel with the first characteristic area.

14. An examination apparatus comprising:

an exclusion area setting unit that sets, with respect to each pixel on a reference pattern image of an examination reference, when a maximum value of image brightness variations within a first predetermined range from a point of a pixel is equal to or less than a first threshold, the point of the pixel to an exclusion area;

a local-area setting unit that sets a local area from among areas excluding the exclusion area in an alignment target area, the local area being an execution target area of local alignment;

a local alignment unit that performs the local alignment a pattern image of an examination target and the reference pattern image, in the local area, to obtain a shift amount that is a result of the local alignment; and a shift unit that shifts a whole of the reference pattern image by using the shift amount.

* * * * *